United States Patent [19]

Binder

[11] Patent Number: 5,587,291
[45] Date of Patent: Dec. 24, 1996

[54] METHOD FOR THE DETERMINATION OF PLASMIN α2-ANTIPLASMIN COMPLEXES AND THE USE OF THIS METHOD AS A MEAN OF DETERMINING CHANGES IN THE FIBRINOLYTIC SYSTEM

[75] Inventor: Bernd Binder, Vienna, Austria

[73] Assignee: Berbi Gesellschaft m.b.H., Vienna, Austria

[21] Appl. No.: 157,210

[22] PCT Filed: Apr. 14, 1993

[86] PCT No.: PCT/AT93/00065

§ 371 Date: Dec. 10, 1993

§ 102(e) Date: Dec. 10, 1993

[87] PCT Pub. No.: WO93/21532

PCT Pub. Date: Oct. 28, 1993

[30] Foreign Application Priority Data

Apr. 14, 1992 [AT] Austria .................................. 772/92

[51] Int. Cl.$^6$ .................. G01N 33/86; G01N 33/577; G01N 33/543
[52] U.S. Cl. .................. 435/7.4; 435/7.92; 435/7.94; 435/13; 435/70.21; 435/240.27; 436/501; 436/529; 436/548; 436/69; 530/388.26
[58] Field of Search .................. 435/7.4, 7.92, 435/7.94, 13, 70.21, 240.27; 436/501, 529, 548, 69; 530/388.26

[56] References Cited

U.S. PATENT DOCUMENTS

| | | | |
|---|---|---|---|
| 4,216,291 | 8/1980 | Collen | 435/7.9 |
| 4,629,694 | 12/1986 | Harpel | 435/13 |
| 4,820,635 | 6/1989 | Sanders et al. | 435/7.4 |

OTHER PUBLICATIONS

Campbell, A. M. Monoclonal Antibody Technology. The Production and Characterization of Rodent and Human Hybridomas. Laboratory Techniques in Biochemistry and Molecular Biology 13: 186–209, 1984.

Collen, D. et al, "Neoantigenic Expression in Enyyme–Inhibitor Complexes: A Means to Demonstrate Activation of Enzyme Systems." Biochemica et Biophysica Acta 525:287–289, 1978.

Kawakami, M. "Elevated Plasma Levels of $\alpha_2$–Plasmin Inhibitor—Plasmin Complex in Patients with Rheumatic Diseases". Arthritis and Rheumatism 32(11) 1427–1433, 1989.

Sevier, E. D. et al. "Monoclonal Antibodies in Clinical Immunology". Clinical Chemistry 27(11):1797–1806, 1981.

Hatty, E. et al. Monoclonal Antibodies Against Plasminogen and Alpha–2–Antiplasmin: Binding to Native and Modified Antigens. Thrombosis Research 45:485–95, 1987.

*Exparte* Erlich, 3 USPQ2d, 1011–1018.

A. Campbell, Monoclonal Antibody Technology (Elsevier, Science Publishers B.V. 1984) pp. V, 186–209.

W. Church et al, "A Kringle–Specific Monoclonal Antibody", Hybridoma 13(5):423–429 (1994).

P. Holvoet et al, "A Monoclonal Antibody Directed Against the High–Affinity Lysine–Binding Site (LBS) of Human Plasminogen", Eur. J. Biochem. 157: 65–69 (1986).

P. Holvoet et al, "An Enzyme–Linked Immunosorbent Assay (ELISA) for the Measurement of Plasmin–α2–Antiplasmin Complex", Thromb. Haemost. 56(2) 124–7, 1986.

F. Leebeek et al, "Plasmin Inhibitors in the Prevention of Systemic Effects During Thrombolytic Therapy", J. Am. Coll. Card. 15(6):1212–20, 1990.

P. Meijer et al., "The Potency of the Fibrinolytic System Detected by a New Assay for α2–Antiplasmin–Plasmin Complex . . . ," Fibrinolysis 6(Supp 3) 94–6 (1992).

H. Pelzer et al, "A Novel Enzyme–Linked Immunoassay (ELISA) for the Determination of α2–Antiplasmin–Plasmin Complex in Human Plasma . . . ", Fibrinolysis 7:69–74 (1993).

H. Pelzer et al, "Determination of α2–Antiplasmin–plasmin complex in Human Plasma . . . ," Fibrinolysis 7:69–74 (1993).

*Primary Examiner*—Carol A. Spiegel
*Attorney, Agent, or Firm*—Herbert Dubno; Jonathan Myers

[57] ABSTRACT

Method for the quantitative determination of plasmin-α2-antiplasmin complexes, using a specific monoclonal antibody directed against the neoantigene in the plasmin-α2-antiplasmin complex, and use of such a method of determining PAP-complexes in plasma and serum to assess changes in the fibrinolytic potential.

5 Claims, 5 Drawing Sheets

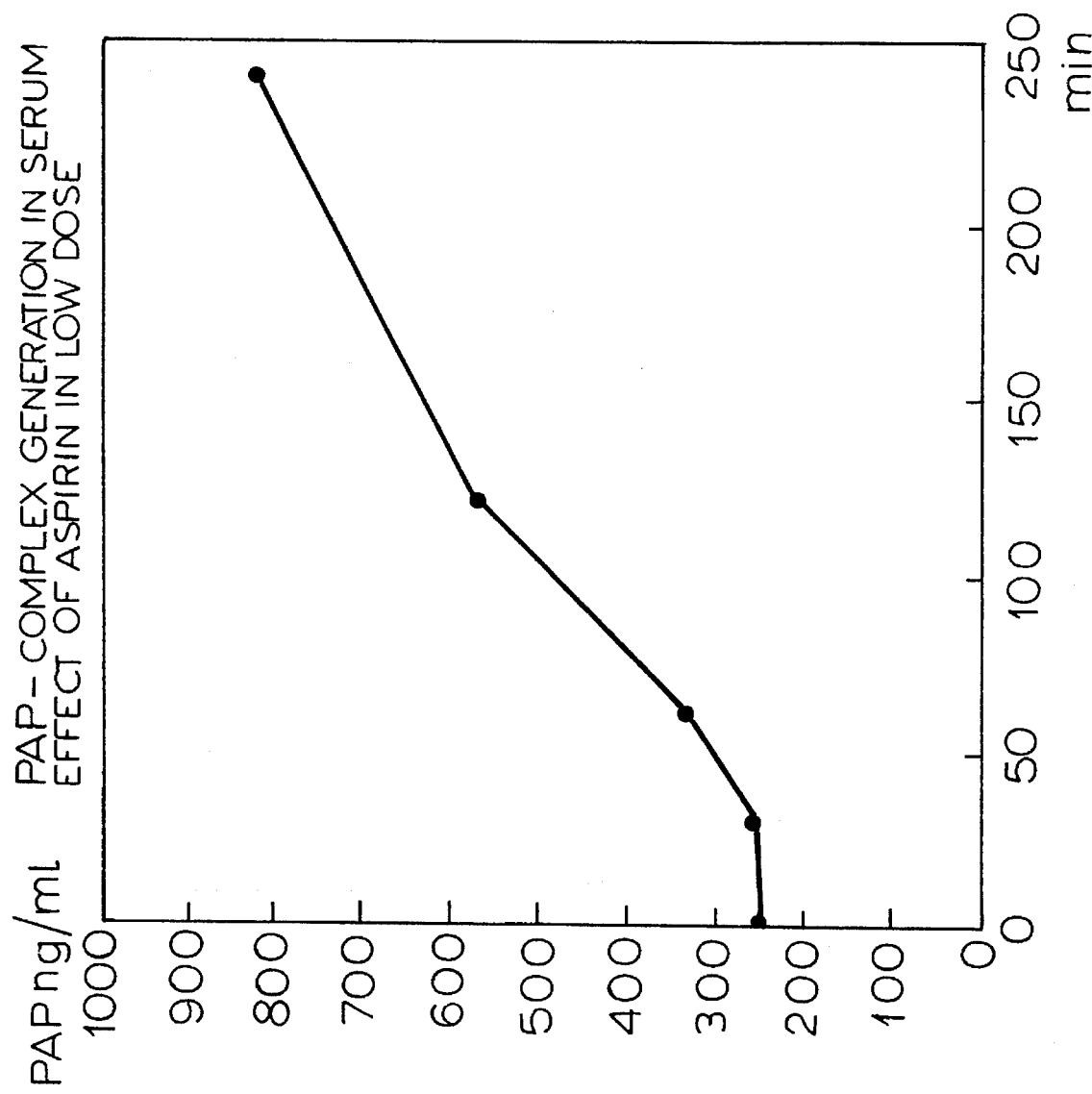

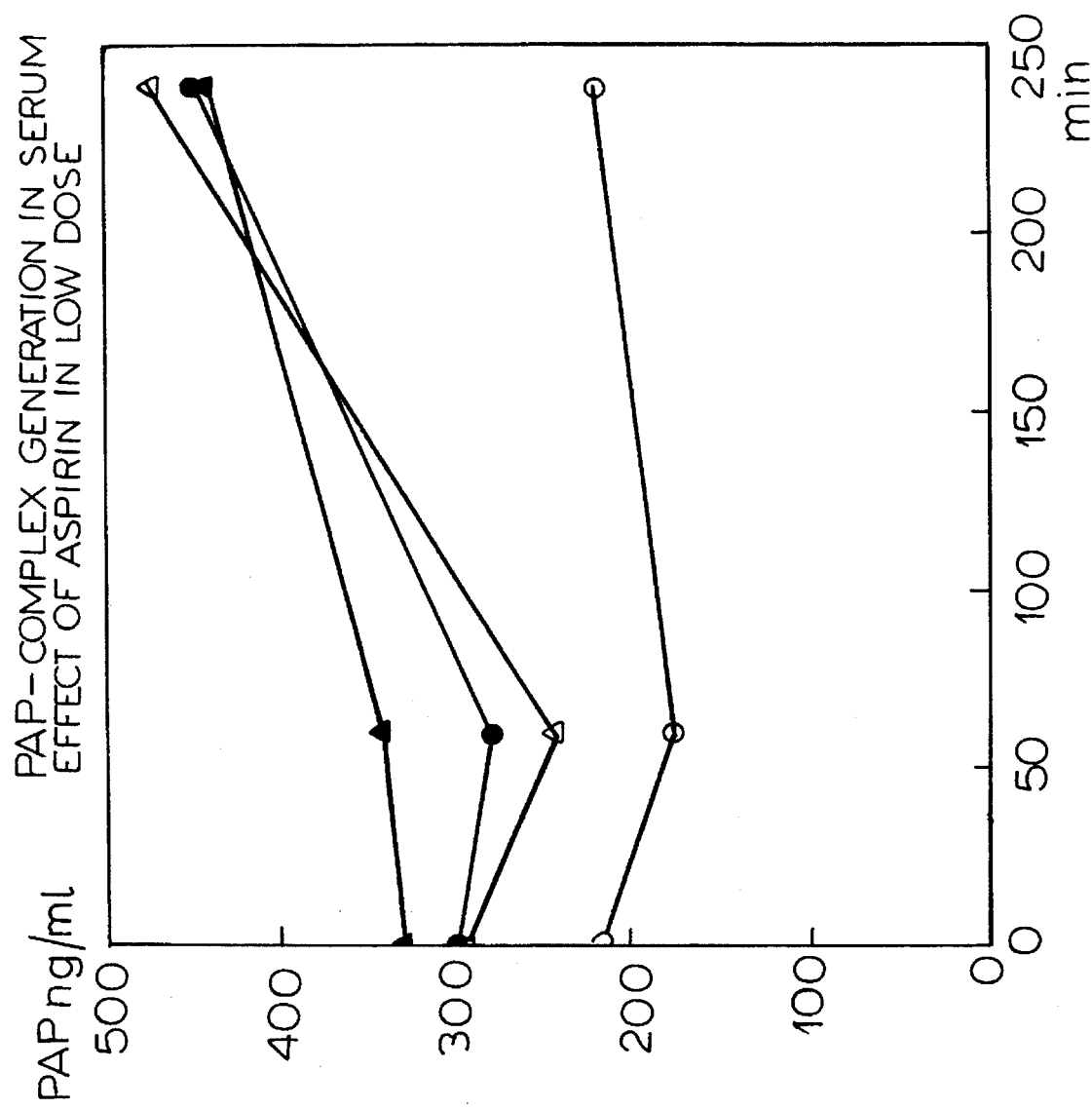

METHOD FOR THE DETERMINATION OF PLASMIN α2-ANTIPLASMIN COMPLEXES AND THE USE OF THIS METHOD AS A MEAN OF DETERMINING CHANGES IN THE FIBRINOLYTIC SYSTEM

BACKGROUND OF THE INVENTION

FIELD OF THE INVENTION

The invention describes a method for the quantitative determination of plasmin-α2-antiplasmin complexes as well as the use of this method as a mean of determining changes in the fibrinolytic system.

Introduction:

α2-antiplasmin is the most important plasmin inhibitor. Its rapid reaction with plasmin results in the formation of an inactive complex composed of one molecule of each component. Two steps are involved in this process: first, a reversible complex is formed between the lysine-binding site of plasmin and complementary sites on the carboxy terminal end of the α2-antiplasmin molecule. In a second step, an irreversible complex is generated associated with the cleavage of a peptide-bond in the inhibitor. During activation of plasminogen to plasmin an equilibrium exists between formation of plasmin-α2-antiplasmin complexes, occurring preferentially in the fluid phase and binding and action of plasmin on the fibrin surface. Bound to fibrin, plasmin is protected against inhibition by α2-antiplasmin. However, whenever fibrin is completely dissolved the plasmin liberated from the fibrin surface is immediately complexed by α2-antiplasmin.

Whenever fibrin forms in circulation, this process will be accompanied by activation of the fibrinolytic system because of the well known effects of fibrin on tissue plasminogen activator (t-PA). Plasmin generated thereby will in part become complexed with α2-antiplasmin leading to increased levels of plasmin-α2-antiplasmin complexes. Such increased levels of PAP-complexes have therefore been found in many circumstances in which fibrin formation is increased as in thrombophilia, hypercoagulability, disseminated intravascular coagulation, endotoxin shock, leukemia, liver diseases, nephrotic syndrome or after major surgery. Even in plasma after venous occlusion in most cases increased plasmin-α2-antiplasmin levels have been found consistent with increased fibrin formation and increased levels of tissue plasminogen activator in the venous occlusion plasma.

It is to be expected that during formation of serum a time dependent generation of PAP complexes occurs. The amount of PAP complexes generated in serum can be expected to be dependent on the amount of other plasminogen activators present in the respective environement as well as on plasminogen activator inhibitors, receptors and binding proteins.

While in all cases mentioned above only a limited increase of PAP levels is observed, thrombolytic therapy leads to extensive activation of the fibrinolytic system to a massive plasmin formation in the fluid phase and maximal PAP complex formation. Especially nonfibrin specific plasminogen activators such as streptokinase or urokinase can cause complete consumption of plasmin inhibitors resulting in an increased bleeding tendency due to plasminemia. Therefore the plasmin activity is no longer restricted to its specific substrate fibrin but can extend to nonspecific substrates as fibrinogen and other coagulation factors. Therefore, determination of plasmin-α2-antiplasmin complexes on the one hand can serve as indicative for general plasminemia during hyperfibrinolytic states with fibrinogen and α2-antiplasmin consumption and possible bleeding tendency; on the other hand, slightly increased levels of plasmin-α2-antiplasmin complexes are indicative for ongoing thrombus formation and thrombus dissolution as in the case of thrombophilia and PAP complexes in serum, respectively and are dependent on the total fibrinolytic potential.

Methods Available for Determination of PAP:

To determine PAP complexes several test methods have been published including two dimensional immunelectrophoresis, latex assay, RIA and more recently ELISA systems. Initially a latex agglutination assay for determination of PAP complexes was introduced by Plow et al. with rather low sensitivity. Then a two dimensional electrophoresis was described using the different mobility of free and complexed α2-antiplasmin. This method was still not sensitive enough and rather time consuming and not applicable for a larger number of samples. Employing polyclonal antisera raised against plasmin B-chain α2-antiplasmin complexes a RIA was developed by Wiman et al. thereby avoiding recognition of intact plasminogen or plasmin. But intact α2-antiplasmin would still be detected together with the PAP complex, though to a much lesser extent.

A great advance was the development of the double sandwich technique used in the ELISA systems. Several methods have been developed since either utilising an antibody against antiplasmin as a catching antibody and an antibody against the enzyme as detecting antibody or vice versa. Harpel et al. first published a sensitive assay with a polyclonal antibody against α2-antiplasmin as catching antibody and POX-labeled Fab-fragments against plasminogen as detecting system, whereby the Fab-fragments are preferred to whole antibodies to reduce unspecific binding of plasminogen and other plasma proteins to immuno-globulins. Other ELISA-systems were described by Holvoet et al. and Mimuro et al. employing either two monoclonal antibodies against either part of the complex or one polyclonal and one monoclonal antibody. Most recently a liposome immune lysis assay (LILA) was introduced by Hasada et al. The ELISA or LILA test systems described up to now have, however, certain limitations because of interference of the abundant amounts of uncomplexed α2-antiplasmin or plasminogen with the rather low concentrations of the PAP complex. All methods described above have, however, the disadvantage of utilising antibodies recognising the complexes as well as the native uncomplexed molecules.

In DE-A1-41 15 993 A method is disclosed for the production of a monoclonal antibody BMA PAP6 and the respective hybridoma cell line (BW PAP6). Said antibody has a specific affinity for plasmin-anti-plasmin complexes and no or very little affinity to the separate components of this complex. This antibody was obtained by immunizing with a plasmin-anti-plasmin complex cleaved by treatment with ammonia. Also, this antibody is only functionally characterized by means of an ELISA but not utilizing a Western Blot

SUMMARY OF THE INVENTION

Therefore, the invention here is a test system employing a specific monoclonal antibody against the neoantigen in the PAP complex. Said antibody was obtained by immunizing with a natural not ammonia-cleaved plasmin-anti-plasmin complex and said antibody furthermore reacts also exclusively with a plasmin-anti-plasmin complex utilizing Western Blot and said antibody is utilized as a catching antibody. Thereby, the respective plasmin-anti-plasmin complex ELISA is also highly specific and sensitive in plasma and serum samples.

Production and characterization of the antibody directed against the mere antigen in the plasmin-anti-plasmin complex.

The antibody utilized in the invention MPW7AP is secreted from the respective hybridoma cell line and the said was deposited at the Public Health Laboratory Service, European Collection of Animal Cell Cultures, Salisbury, UK, with the Number 94072843. The hybridoma cell line was obtained according to published methods by fusion of spleen cells of a mouse immunized with the native plasmin-anti-plasmin complexe with a mouse myeloma cell line (NS0). The secreted monoclonal antibody is characterized by a specific reaction exclusively with plasmin-anti-plasmin complexes but not with the respective separate components utilizing Western Blot technique (FIG. 1).

Test Principle

The test described here is a solid phase enzyme immunoassay in which MPW7AP, a specific monoclonal antibody directed against the neoantigen of the PAP-complex is adsorbed on plastic microtiter plates. During incubation with test samples PAP-complexes are selectively bound and after washing away unbound material the complexes are detected by MPW2PG POX, a peroxidase-labelled monoclonal antibody against the kringle 1-3 region of the plasminogen part of the complex. Quantification of labelled antigen-antibody conjugates is achieved by ABTS, a chromogenic substrate for peroxidase.

Material and Equipment 96-well flat bottom microtiter plates with high binding capacity (e.g. NUNC immunoplate maxisorp 4-93454 or GREINER ELISA plates (No. 655061), plate sealers (e.g. COSTAR 3095).

ELISA reader for 405 nm and 492 nm wavelength (e.g. Anthos reader 2001, Zinsser Austria)

Antibody to PAP neoantigen MPW7AP and antibody to kringle 1-3 region of plasminogen Pox-labelled, MPW2PG POX (Technoclone, Vienna, Austria)

PAP complex standard plasma and PAP complex depleted plasma (Technoclone, Vienna, Austria)

ABTS 2-2' azinobis(3-ethylbenz-thiazolinesulfonic acid) from Boehringer Mannheim, Germany Aprotinin (TRASYLOL®) from Bayer, Leverkusen Germany 2-ethylmercury-thio]-benzoic acid sodium salt (THIMEROSAL®) 818957, Merck, Germany polyoxyethylenesorbitan monooleate (Tween 20$^R$) P 13 79, Sigma, U.S.A.

serum albumin bovine, purified (BSA) ORHO 20/21, Behring, Germany benzamidiniumchloride 820122, Merck Germany Solutions Coating buffer: 1.59 g Na2CO3.10H2O, 2.93 g NaHCO3 100 mg THIMEROSAL® with distilled water to 1l, pH 9.6.

Coating solution: 20 µg/ml MPW7AP in coating buffer; 100 µl/well

Phosphate buffered saline (PBS): 8 g NaCl, 0.2 g KH2PO4, 1.44 g Na2HPO4.2H2O with distilled water to 1l, pH 7.4

Washing buffer: PBS+0.5% Tween 20

Blocking solution: PBS+1% BSA

Dilution buffer 1 (DB1): PBS+1% BSA+2000 KIU/ml aprotinin+20 mM benzamidinium chloride or a specific inhibitor for t-PA, e.g. PPACK Dilution buffer 2 (DB2): DB1+1% PAP depleted plasma Dilution buffer 3 (DB3): DB1+10% PAP depleted plasma Detecting solution: 10 µg/ml MPW2PG Pox in DB1; 100 µl/well Substrate buffer: 1.29 g citric acid monohydrate, 1.375 g Na2HPO4.2H2O with distilled water to 100 ml, pH 4.0

Substrate solution: 1 mg ABTS/ml solution+1 µl H2O2 30%/ml solution in substrate buffer; 100 µl/well Stop solution: 320 mg NaF/100 ml distilled water; 100 µl/well Stability of the Reagents:

Coating buffer and coated plates containing an antimicrobial substance are stable at 4° C. Other protein containing solutions and washing buffer should be prepared freshly or kept under sterile conditions to prevent microbial growth. Antibiotics should not be used in these cases to avoid adverse reactions with the peroxidase.

Procedure:

Preparation of plates:

The wells of an ELISA plate are filled with 100 µl/well coating solution, preferably by use of a multichannel micropipette. The plate should remain covered with a self-adhesive plastic foil for at least 16 h at 4° C. but can also be stored that way for prolonged time. Before use, the plate is emptied and refilled with 100 µl/well of blocking solution and incubated for 1 h at 37° C. to block excessive reactive groups on the plate surface. For all incubation steps the plate remains covered with the plastic foil.

Sample Preparation:

Normal citrated or EDTA plasma can be used but one should be aware that uninhibited plasminogen activators will lead to in vitro formation of PAP complexes. Especially in monitoring thrombolytic therapy, blood samples should therefore always be collected using anticoagulants containing inhibitors e.g. 2000 KIU/ml aprotinin+20 mM benzamidine final concentration. The plasma samples are diluted 1:10 in DB1 for low concentrations and 1:100 for high concentrations of PAP complexes. 100 µl/well are needed and at least duplicate determinations are recommended.

Standard Preparation:

PAP complex standard plasma is reconstituted with distilled water. Serial dilutions from 1:100 to 1:800 and blanks are prepared in DB3 for use with low PAP concentration samples and in DB2 for use with samples containing high PAP concentrations. Also 100 µl/well and duplicates are necessary.

Washing of the Plates:

Between all incubation steps the plates are washed three times with approximately 300 µl/well washing buffer either manually or by use of an automatic plate washer. After each emptying step the plate is carefully tapped dry on absorbent paper towels.

Flow Sheet of Procedure:

1. Coating of ELISA plates overnight at 4° C.
2. incubation with blocking solution 1 h at 37° C.
3. washing step
4. incubation of samples overnight at 4° C.
5. washing step
6. incubation with detecting solution 2 h at 37° C.
7. washing step 8. incubation with substrate solution 30 min at room temperature, protected from light
9. addition of stop solution
10. plotting of standard values on linear scale and reading of sample values from the respective standard curve for high and low PAP concentrations; multiplication with the dilution factor.

Evaluation of Results:

For evaluation of the results, the reading of the samples are compared with those of a reference PAP complex preparation.

Standardisation:

Since plasmin-α2-antiplasmin complexes are not easily prepared in a stable purified form—the complex is susceptible to proteolytic degradation and different epitopes might be generated whether the complex is formed in excess of plasmin or of inhibitor (1)—we decided to prepare PAP complexes directly in plasma and to calibrate them with PAP complexes generated from purified components. For this purpose citrated plasma was incubated with more than saturating concentrations of urokinase to produce maximum amount of plasmin-α2-antiplasmin complexes. Thereafter the reaction was terminated by addition of benzamidine and TRASYLOL®. The so formed complexes are stable either frozen at −70° C. or lyophilized at 4° C. To determine the actual amount of complexes in the standard plasma the readings in the ELISA assay were compared with those of PAP complexes generated from purified components. For this purpose plasmin was prepared freshly from purified Glu-plasminogen by incubation with urokinase bound to SEPHAROSE™(beaded agarose) and after removal of urokinase SEPHAROSE™ the resulting plasmin activity was determined with S-2251 immediately and after 30 min incubation with purified α2-antiplasmin at 37° C. The differences in plasmin activity represents the amount of PAP complexes formed (FIG. 2).

Specificity:

The described test is specific for plasmin-α2-antiplasmin complexes and allows full plasma recovery provided the standard was diluted in PAP- depleted plasma in the same concentration as the plasma samples to be tested.

Sensitivity and Normal Values:

In this assay the lower detection limit is 10 ng/ml in purified systems as well as in plasma.

Normal Values:

In a normal control population mean PAP values in citrated plasma are 152±72 ng/ml and 132±72 ng/ml in EDTA plasma; in serum samples PAP values are mostly increased.

Pathological Values:

Thrombolytic therapy results in PAP plasma values of >800 ng/ml. In patients with coronary heart disease treated successfully by percutaneous transluminal coronary angiography (PTCA) PAP values were found to be increased 12 months thereafter (FIG. 3).

| Determination of PAP complexes in different groups of patients: | | |
| --- | --- | --- |
| Method | Patients | Plasma levels |
| crossed immune electrophoresis | Disseminated intravascular coagulation | ++ |
| | Carcinoma/Leukaemia | ++ |
| RIA | Cancer[4] | 1.2–3.6 µg/ml |
| | Surgical patients | 2.1 µg/ml |
| | "high fibrinogen" patients | 2.1 µg/ml |
| | PAP Levels are of predictive value for postoperative deep vein thrombosis | |
| ELISA | Carcinomas | 0.12–0.15 µM |
| | Acute promyeloic | >0.28 µM |
| | Hemorrhagic shock | >0.28 µM |
| | Sepsis | 0.24 µM |
| ELISA | Liver disease or hepatic failure | 0.7 µg/ml |
| | DIC | 6.9 µg/ml |
| | Acute promyeloic leukemia | 11.5 µg/ml |
| | Shock | 14.1 µg/ml |
| | Sepsis | 2.2 µg/ml |
| | Thrombotic thrombocytopenic pupura | 2.1 µg/ml |
| | Septic lupus erythematoides | increased |

PAP Complexes in Serum:

When serum is harvested after different times after blood collection and PAP complexes are determined in the obtained serum samples, it can be shown that in a certain group of people the time dependent increase in the amount of the plasmin-anti-plasmin complexes is seen (FIG. 4). One of these groups showing such a plasmin-anti-plasmin increase in serum are persons, which show an altered fibrinolytic potential, for e.g. due to the intake of the Aspirin (acetylsalicylic acid)

Thereby, the daily intake of for e.g. 100 mg Aspirin causes after one week a significant increase in PAP complexes, which after a two week intake is even further increased. One week after cessation of Aspirin, the increase in the PAP complexes is less pronounced but still detectable (FIG. 5).

Control and Calibration Procedures:

There is no PAP standard available at the moment. Therefore, standardization can be done by generating PAP complexes from purified components and calibrate with such a standard preparation plasma samples containing PAP complexes because of the higher stability of PAP complexes in plasma.

| Comparison to data obtained by others:* | | |
| --- | --- | --- |
| | Normal plasma | Fully activated plasma |
| Latex agglutination (only titer) | 1:4 | 1:512 |
| Crossed immunelectrophoresis semiquantitative (0 to +++) | 0 | +++ |
| Radioimmunoassay lower limit 1.5 µg/ml | 0–2 µg/ml | n.d. |
| ELISA30 anti α2-AP as catching antibody antiplasminogen F(ab)2 as detecting antibody | 4.1–3.5 fmol/ml plasmin equivalent | 177.6 fmol/ml |
| ELISA** anti plasminogen (polyclonal) catching | | |

-continued

Comparison to data obtained by others:*

| | Normal plasma | Fully activated plasma |
|---|---|---|
| antibody, anti α2-AP monoclonal as detecting antibody | 0.2 ± 0.1 µg/ml | n.d. |
| LILA (same system as above) | 0.8 ± 0.4 µg/ml | n.d. |
| ELISA *** anti neoantigen monoclonal as catching antibody antiplasminogen monoclonal as detecting antibody | 152 ± 72 ng/ml | >1 µg/ml |

*No direct comparison of test systems could be performed because of a lack of availability of several reagents.
**This system corresponds to a PAP kit commercially available from Teijin
***Matter of this invention

BRIEF DESCRIPTION OF THE DRAWING

FIG. 4 Time is a graph which plots the time of plasmin-anti-plasmin complex formation against concentration in the serum of a reactive patient undergoing therapy with aspirin FIG. 5 is a set of four graphs which plot the time of generation of plasmin-anti-plasmin complexes in serum (0–4 Hours) before (o) one week (●) two weeks (▲) after initiation of Aspirin treatment and one week after cessation of Aspirin treatment (Δ).

Figure 1:
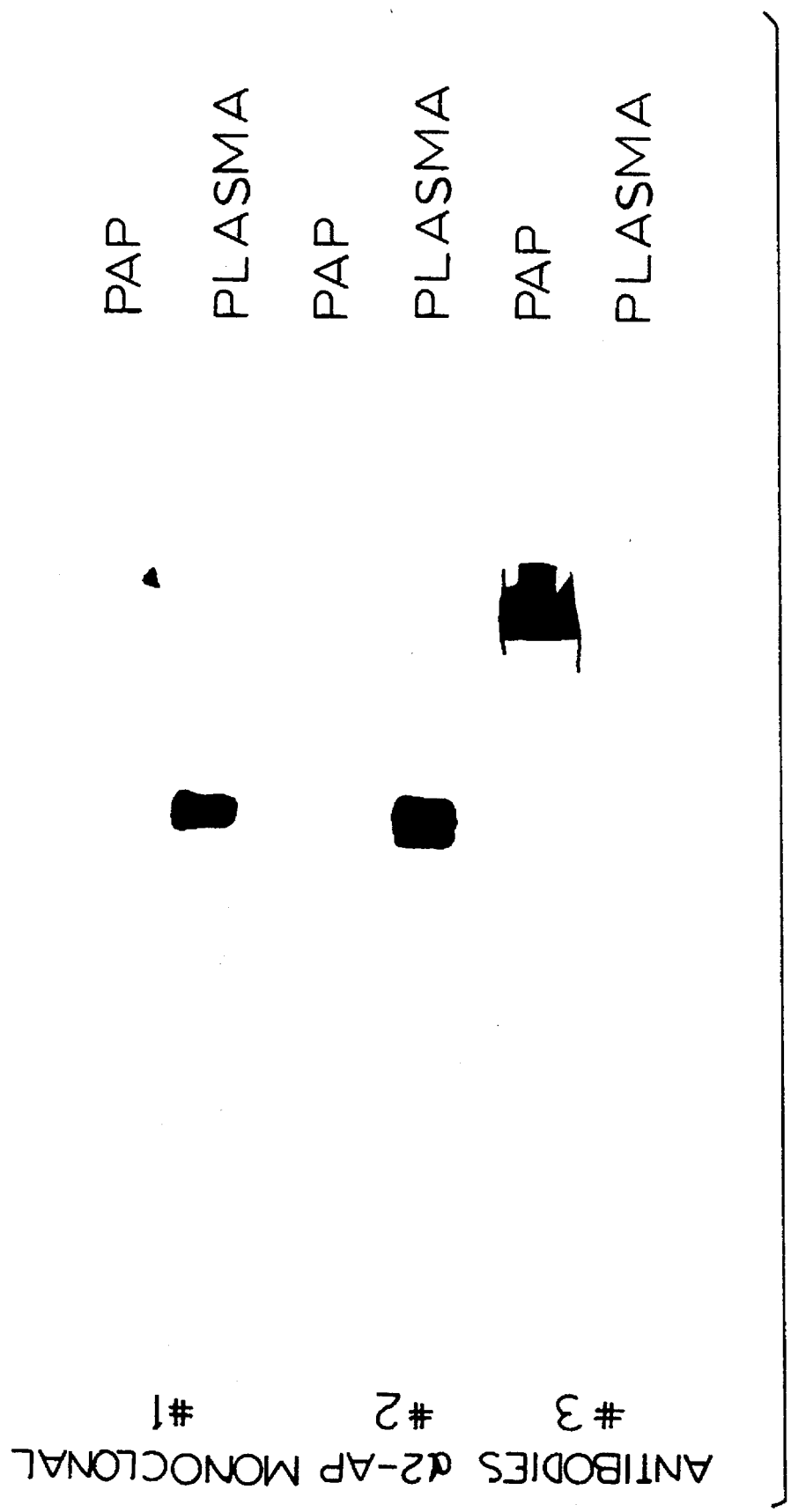
FIG. 1 is Western Blot analysis of 3 monoclonal antibodies using α2-antiplasmin, one of the components of the plasmin-anti-plasmin complex as antigen. Antibody 3 is Antibody MPW7AP
Figure 2:
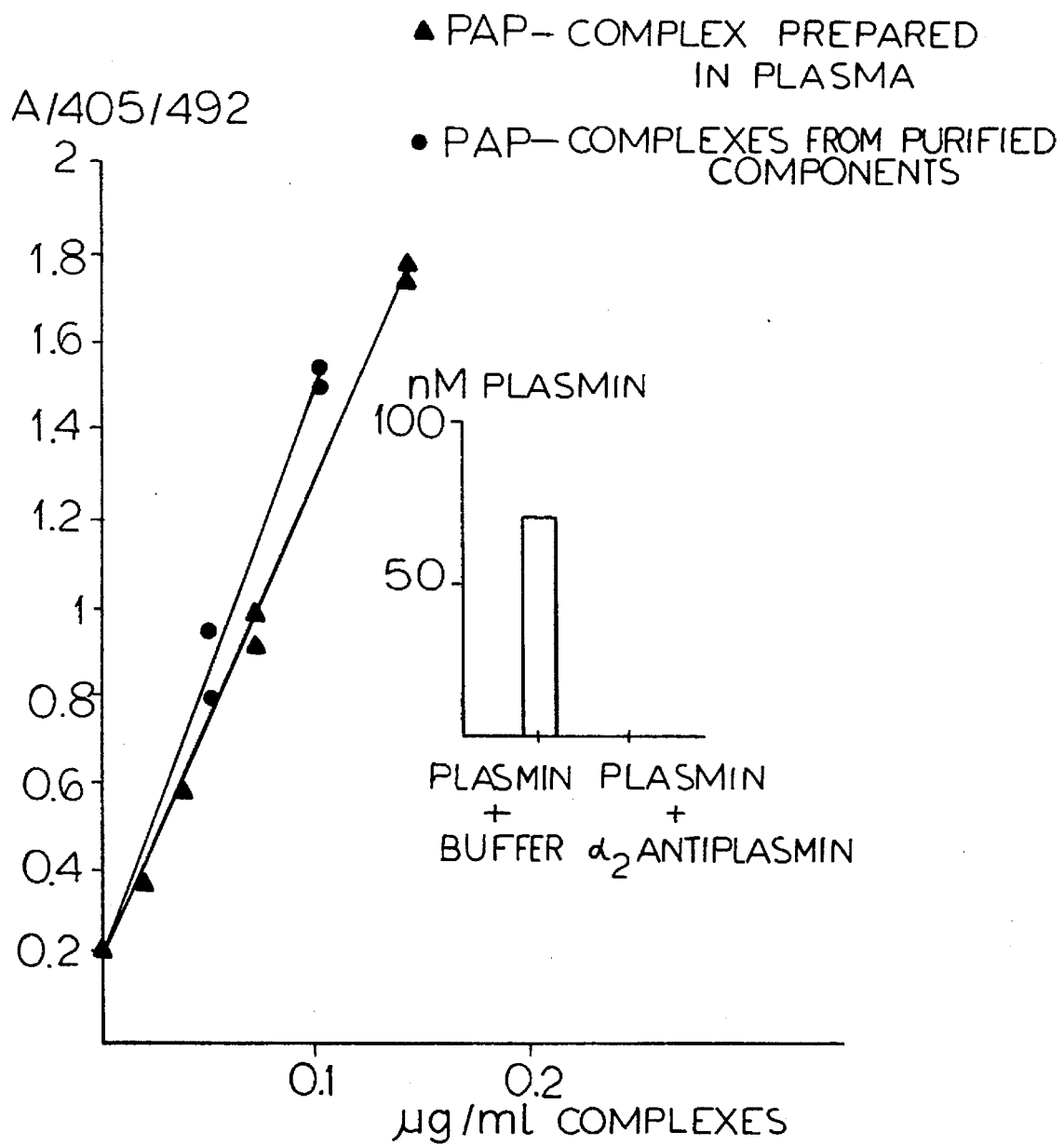
FIG. 2 is a graph which compares PAP complexes prepared in plasma with PAP complexes from purified components. In the insert the amidolytic determination of plasmin activity from freshly prepared plasmin incubated with buffer or without excess α2-antiplasmin is shown. From the differences in plasmin activity (plasmin inhibited) the concentration of found complexes is calculated.
Figure 3:
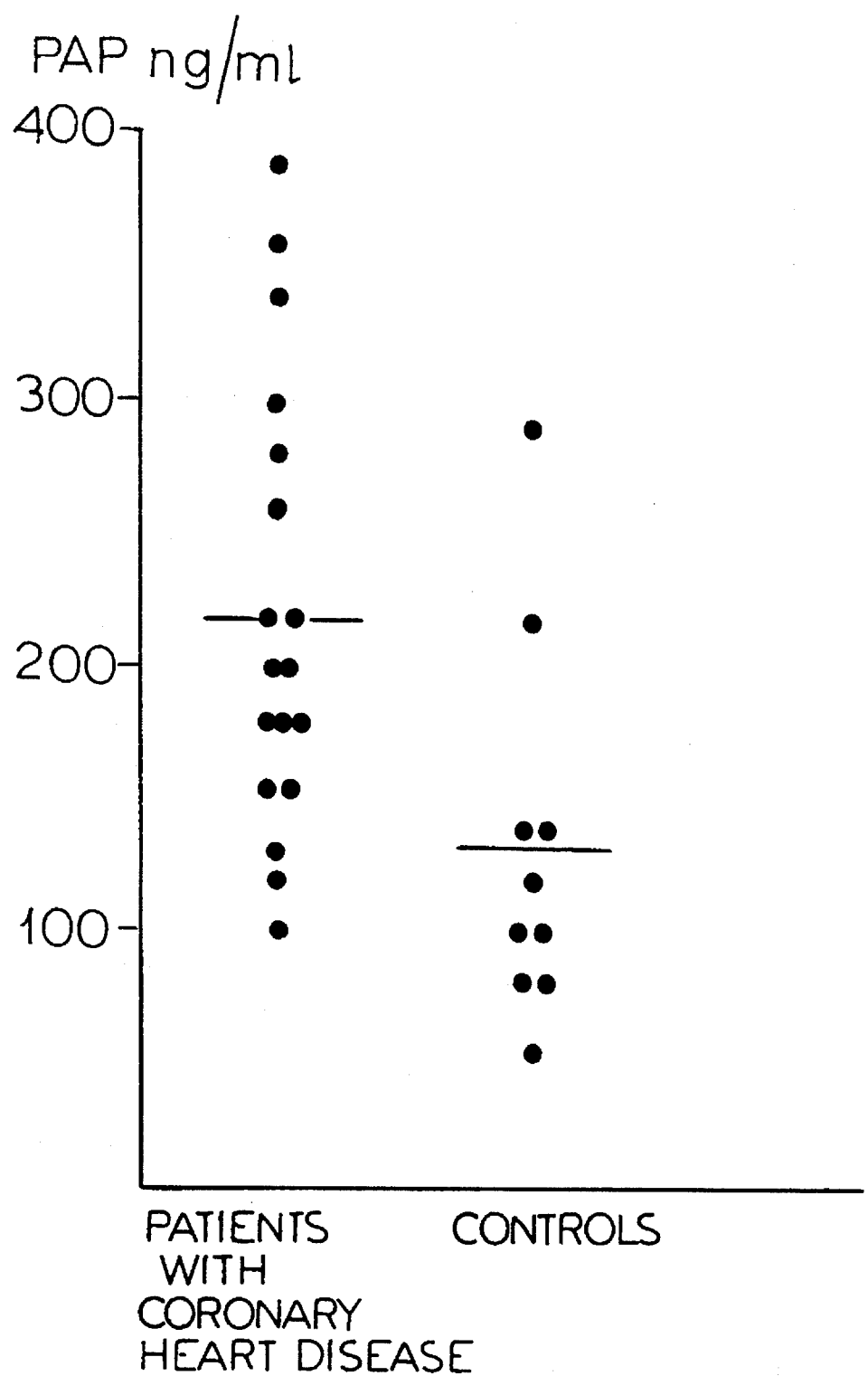
FIG. 3 is a graph which compares PAP-complexes in controls and in patients with coronary heart disease.

I claim:

1. A composition comprising a hybrid continuous cell line having ECACC deposit no. 94072834 that produces monoclonal antibody MPW7AP against a neoantigen in a natural, non-ammonia cleaved plasmin-alpha2-antiplasmin (PAP) complex, said monoclonal antibody MPW7AP characterized by a specific reaction exclusively with PAP complex but not with the respective components in a Western blot analysis, which comprises a cell hybrid of a mouse spleen cell immunized with the PAP complex, fused to a mouse myeloma.

2. Monoclonal antibody MPW7AP produced by a hybrid continuous cell line having ECACC deposit no. 94072834.

3. A process for the quantitative determination of a plasmin-alpha2-antiplasmin (PAP) complex in a sample of serum or plasma using a sandwich ELISA system, which comprises the steps of:

(a) obtaining the sample of serum or plasma containing the PAP complex;

(b) providing monoclonal antibody MPW7AP produced by a hybrid continuous cell line having ECACC deposit no. 94072834 as a capture antibody, said capture antibody being immobilized on a solid phase and binding to a neoantigen on the PAP complex, said monoclonal antibody MPW7AP characterized by a specific reaction exclusively with the PAP complex but not with the respective separate components in a Western blot analysis;

(c) capturing the PAP complex by contacting the sample of serum or plasma with said solid phase immobilized capture antibody;

(d) contacting the captured PAP complex with a predetermined amount of an enzyme-labelled detecting antibody which specifically binds to the kringle 1-3 region of the plasminogen part of the PAP complex;

(e) measuring the amount of enzyme label contained in the enzyme-labelled detecting antibody bound to the kringle 1-3 region of the plasminogen part of the captured PAP complex; and (f) comparing the amount of bound label in step (e) with the amount of bound label from a standard with a known amount of said PAP complex, also measured according to steps (b) through (e) in order to quantitatively determine the amount of PAP complex in the sample of serum or plasma.

4. The process defined in claim 3 wherein the sample of serum or plasma is serum.

5. A method of evalutating a change in a patient's fibrinolytic system which comprises the steps of:

(a) harvesting a sample of the patient's serum or plasma containing plasmin-$\alpha_2$-antiplasmin (PAP) complex at a given time;

(b) providing monoclonal antibody MPW7AP produced by a hybrid continuous cell line having ECACC deposit no. 94072834 as a capture antibody, said capture antibody being immobilized on a solid phase and binding to a neoantigen on the PAP complex, said monoclonal antibody MPW7AP characterized by a specific reaction exclusively with the PAP complex but not with the respective separate components in a Western blot analysis;

(c) capturing the PAP complex by contacting the sample of serum or plasma with said solid phase immobilized capture antibody;

(d) contacting the captured PAP complex with a predetermined amount of an enzyme-labelled detecting antibody which specifically binds to the kringle 1-3 region of the plasminogen part of the PAP complex;

(e) measuring the amount of enzyme label contained in the enzyme-labelled detecting antibody bound to the kringle 1-3 region of the plasminogen part of the captured PAP complex;

(f) harvesting a second sample of the patient's serum or plasma containing the PAP complex at a later time than the harvesting time given in step (a) and repeating steps (b), (c), (d) and (e) on said second sample; and (g) comparing the amount of bound label in step (e) with the amount of bound label in step (f) in order to quantitatively determine any change in the amount of the PAP complex between the two samples of serum or plasma, and correlating the change in the amount of the PAP complex between said samples to a change in the fibrinolytic system of the patient, wherein increased amounts of PAP complex indicates increased activation of the fibrinolytic system.

* * * * *